(12) United States Patent
Yue

(10) Patent No.: US 7,297,560 B2
(45) Date of Patent: Nov. 20, 2007

(54) METHOD AND APPARATUS FOR DETECTING ENDPOINT

(75) Inventor: Hongyu Yue, Plano, TX (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 10/531,468

(22) PCT Filed: Oct. 31, 2003

(86) PCT No.: PCT/US03/31529

§ 371 (c)(1),
(2), (4) Date: Apr. 15, 2005

(87) PCT Pub. No.: WO2004/042803

PCT Pub. Date: May 21, 2004

(65) Prior Publication Data

US 2006/0037938 A1 Feb. 23, 2006

Related U.S. Application Data

(60) Provisional application No. 60/422,510, filed on Oct. 31, 2002.

(51) Int. Cl.
*H01L 21/00* (2006.01)
(52) U.S. Cl. .......................... 438/9; 438/706; 438/714; 216/60

(58) Field of Classification Search .................... 438/8, 438/9, 706, 710, 712, 714; 216/60, 61
See application file for complete search history.

(56) References Cited

U.S. PATENT DOCUMENTS

| 5,045,149 | A  | * | 9/1991  | Nulty ........................... 438/16 |
| 5,251,006 | A  | * | 10/1993 | Honigs et al. .............. 356/319 |
| 5,949,804 | A  | * | 9/1999  | Okazaki ....................... 372/32 |
| 6,137,104 | A  | * | 10/2000 | Webb et al. ................. 250/226 |
| 6,231,774 | B1 |   | 5/2001  | Saito |
| 6,297,064 | B1 | * | 10/2001 | Koshimizu ..................... 438/9 |
| 6,596,551 | B1 |   | 7/2003  | Usui et al. |
| 6,830,939 | B2 | * | 12/2004 | Harvey et al. ................. 438/8 |
| 2003/0003607 | A1 | * | 1/2003 | Kagoshima et al. .......... 438/14 |
| 2004/0004708 | A1 | * | 1/2004 | Willis ........................... 356/72 |
| 2004/0045934 | A1 | * | 3/2004 | Harvey et al. ................ 216/60 |

* cited by examiner

*Primary Examiner*—Kin-Chan Chen
(74) *Attorney, Agent, or Firm*—Oblon, Spivak, McClelland, Maier & Neustadt, P.C.

(57) ABSTRACT

The present invention presents a method for detecting an endpoint of an etch process for etching a substrate in plasma processing system (1) comprising: etching the substrate; measuring at least one endpoint signal; generating at least one filtered endpoint signal by filtering the at least one endpoint signal, wherein the filtering comprises applying a Savitsky Golay filter (12) to the at least one endpoint signal; and determining (14) an endpoint of the etch process from the at least one filtered endpoint signal.

32 Claims, 11 Drawing Sheets

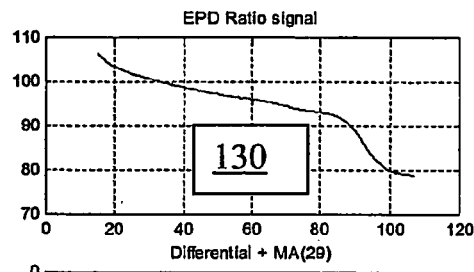
FIG. 9A1
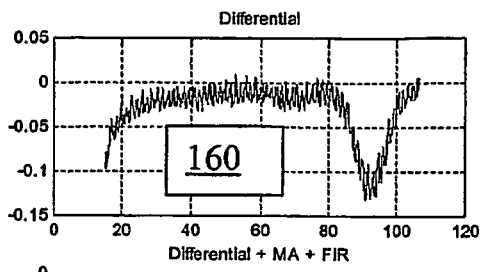
FIG. 9A2
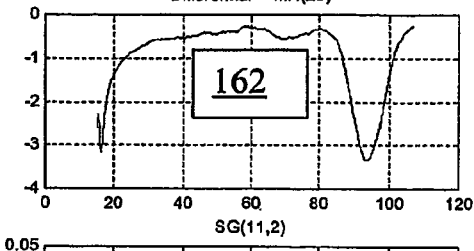
FIG. 9B1
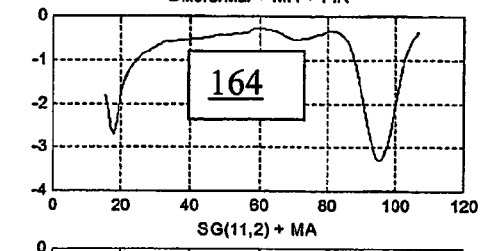
FIG. 9B2
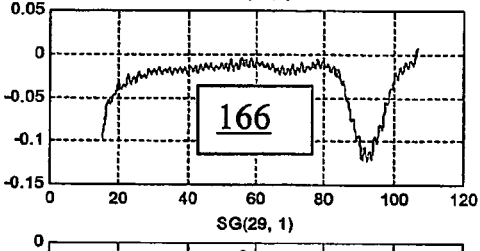
FIG. 9C1
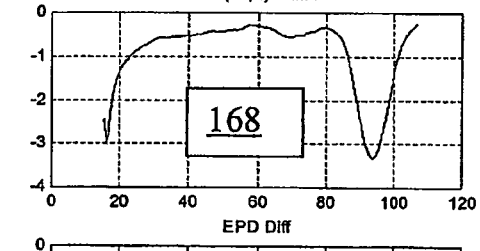
FIG. 9C2
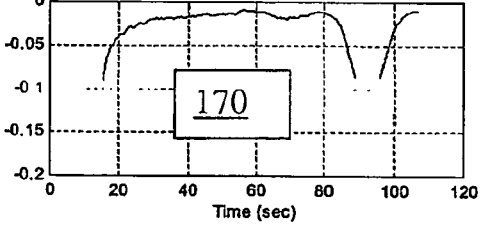
FIG. 9D1
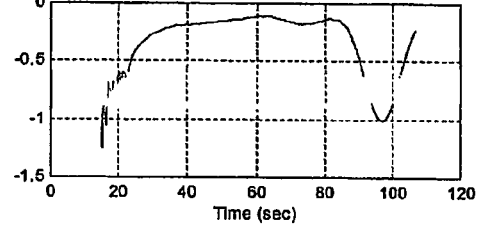
FIG. 9D2

METHOD AND APPARATUS FOR DETECTING ENDPOINT

CROSS-REFERENCE TO RELATED APPLICATIONS

This application claims priority to U.S. Provisional Application Ser. No. 60/422,510, filed Oct. 31, 2002, and is related to co-pending application 60/422,511, entitled "Method and apparatus for determining an etch property," filed on Oct. 31, 2002. The contents of these applications are incorporated herein by reference.

BACKGROUND OF THE INVENTION

1. Field of the Invention

The present invention relates to a method and apparatus for plasma processing a substrate, and more particularly to an improved method for determining an endpoint during a plasma etch process.

2. Discussion of the Background

Typically, during semiconductor processing, a (dry) plasma etch process is utilized to remove or etch material along fine lines or within vias or contacts patterned on a silicon substrate. The plasma etch process generally involves positioning a semiconductor substrate with an overlying patterned, protective layer, for example a photoresist layer, into a processing chamber. Once the substrate is positioned within the chamber, an ionizable, dissociative gas mixture is introduced within the chamber at a pre-specified flow rate, while a vacuum pump is throttled to achieve an ambient process pressure. Thereafter, a plasma is formed when a fraction of the gas species present are ionized by electrons heated via the transfer of radio frequency (RF) power either inductively or capacitively, or microwave power using, for example, electron cyclotron resonance (ECR). Moreover, the heated electrons serve to dissociate some species of the ambient gas species and create reactant specie(s) suitable for the exposed surface etch chemistry.

Once the plasma is formed, selected surfaces of the substrate are etched by the plasma. The process is adjusted to achieve optimal conditions, including an appropriate concentration of desirable reactant and ion populations to etch various features (e.g., trenches, vias, contacts, etc.) in the selected regions of substrate. Such substrate materials where etching is required include silicon dioxide ($SiO_2$), low-k dielectric materials, poly-silicon, and silicon nitride. As the feature size shrinks and the number and complexity of the etch process steps used during integrated circuit (IC) fabrication escalate, the requirements for tight process control become more stringent.

Consequently, real time monitoring and control of such processes becomes increasingly important in the manufacture of semiconductor ICs. For example, one such monitoring and control diagnostic necessary for the timely completion of an etch step or process is endpoint detection. Endpoint detection refers to the control of an etch step and, in particular, to the detection of the feature etch completion or the instant in time when the etch front reaches the etch stop layer. If the etch process endpoint is improperly detected, then severe under-cutting of the feature may occur due to over-etching or partially complete features may result due to under-etching. As a result, poor endpoint detection could lead to devices of poor quality that are subject to increased risk of failure. Therefore, the accurate and precise completion of an etch process is an important area for concern during the manufacturing process.

One approach used for endpoint detection is to monitor the emission intensity of light at a pre-specified wavelength in time using optical emission spectroscopy (OES). Such a method might identify a wavelength corresponding to a chemical species present in the etch process that shows a pronounced transition at the etch process endpoint. Subsequently, a resultant signal is analyzed to detect distinct variations in the emission intensity, and the analysis of the resulting signal is then used to correlate with the completion of an etch process. Typically, the species selected corresponds to a reactive species or a volatile etch product. For example, the selected wavelength may correspond to $CO^*$ emission when etching $SiO_2$ and polymer films, $N_2^*$ or $CN^*$ emission when etching nitride films, $SiF^*$ emission when etching poly-silicon and $AlCl^*$ emission when etching aluminum.

In addition to the approach of monitoring the emission intensity at a single wavelength as described above, another approach is to monitor the light intensity at two wavelengths and record the ratio (or some mathematical manipulation thereof) of the two intensities. For instance, one wavelength is chosen for a specie whose concentration decays at an endpoint and a second wavelength is chosen for a specie whose concentration increases at the endpoint. Therefore, the ratio gives improved signal to noise.

SUMMARY OF THE INVENTION

The present invention provides a method for determining an endpoint during an etch process, wherein the method advantageously address the above-identified shortcomings.

It is an object of the present invention to provide a method for detecting an endpoint of an etch process for etching a substrate in a plasma processing system comprising: etching the substrate; measuring at least one endpoint signal; generating at least one filtered endpoint signal by filtering the at least one endpoint signal, wherein the filtering comprises applying a Savitsky Golay filter to the at least one endpoint signal; and determining an endpoint of the etch process from the at least one filtered endpoint signal.

It is another object of the present invention to provide a method for detecting an endpoint of an etch process for etching a substrate comprising: etching the substrate; measuring a first endpoint signal; measuring a second endpoint signal; determining a ratio signal from a ratio of the first endpoint signal and the second endpoint signal, the ratio signal comprises an endpoint transition; determining a differential signal from the ratio signal by applying a differential filter to the ratio signal, wherein the differential filter comprises a Savitsky Golay filter; and determining an endpoint of the etch process from the differential signal.

It is another object of the present invention to provide a plasma processing system comprising: a process chamber; a diagnostic system coupled to the process chamber and configured to measure at least one endpoint signal; and a controller coupled to the diagnostic system, configured to filter the at least one endpoint signal using a Savitsky Golay filter, and configured to determine an endpoint from the at least one filtered endpoint signal.

BRIEF DESCRIPTION OF THE DRAWINGS

These and other advantages of the invention will become more apparent and more readily appreciated from the following detailed description of the exemplary embodiments of the invention taken in conjunction with the accompanying drawings, where:

FIGS. 9A1-9D1 and 9A2-9D2 illustrate an application of a Savitsky Golay (SG) filter to endpoint signals according to an embodiment of the present invention;

DETAILED DESCRIPTION OF THE EMBODIMENT

Figure 1:
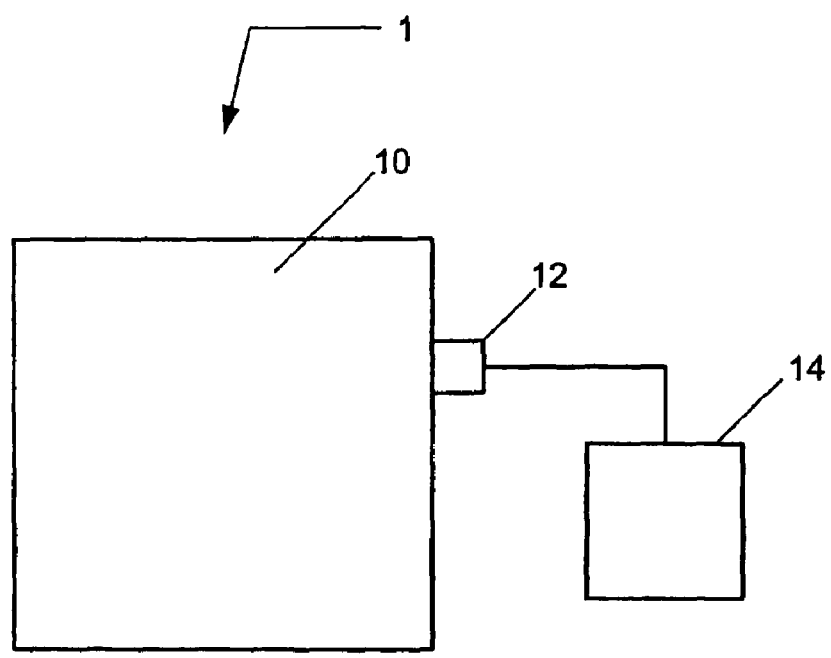
FIG. 1 shows a simplified block diagram of a plasma processing system according to an embodiment of the present invention.

According to an embodiment of the present invention, a plasma processing system 1 is depicted in FIG. 1 comprising a plasma processing chamber 10, a diagnostic system 12 coupled to the process chamber 10, and a controller 14 coupled to the diagnostic system 12. The controller 14 is configured to receive at least one endpoint signal from the diagnostic system 12 and to post-process the at least one endpoint signal in order to accurately determine an endpoint for the process. In the illustrated embodiment, plasma processing system 1, depicted in FIG. 1, utilizes a plasma for material processing. Desirably, plasma processing system 1 comprises an etch chamber.

Figure 2:
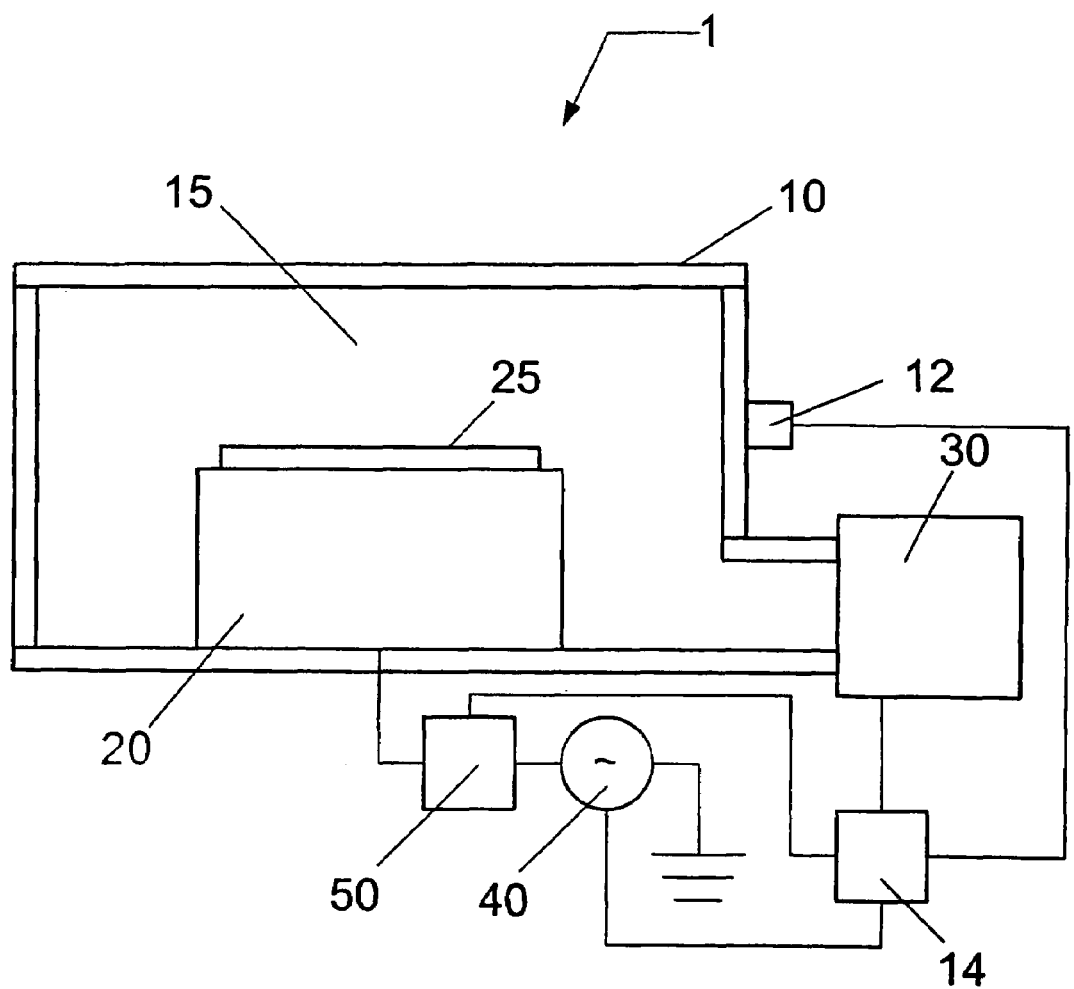
FIG. 2 shows a schematic diagram of a plasma processing system according to another embodiment of the present invention.

According to the illustrated embodiment of the present invention depicted in FIG. 2, plasma processing system 1 can comprise plasma processing chamber 10, substrate holder 20, upon which a substrate 25 (e.g., a semiconductor wafer or a liquid crystal display panel) to be processed is affixed, and vacuum pumping system 30. Substrate 25 can be, for example, a semiconductor substrate, a wafer or a liquid crystal display. Plasma processing chamber 10 can be, for example, configured to facilitate the generation of plasma in processing region 15 adjacent a surface of substrate 25. An ionizable gas or mixture of gases is introduced via gas injection system (not shown) and the process pressure is adjusted. For example, a control mechanism (not shown) can be used to throttle the vacuum pumping system 30. Desirably, plasma is utilized to create materials specific to a pre-determined materials process, and to aid the removal of material from the exposed surfaces of substrate 25. The plasma processing system 1 can be configured to process 200 mm substrates, 300 mm substrates, or larger.

Substrate 25 can be, for example, transferred into and out of plasma processing chamber 10 through a slot valve (not shown) and chamber feed-through (not shown) via robotic substrate transfer system where it is received by substrate lift pins (not shown) housed within substrate holder 20 and mechanically translated by devices housed therein. Once substrate 25 is received from substrate transfer system, it is lowered to an upper surface of substrate holder 20.

Substrate 25 can be, for example, affixed to the substrate holder 20 via an electrostatic clamping system. Furthermore, substrate holder 20 can, for example, further include a cooling system including a re-circulating coolant flow that receives heat from substrate holder 20 and transfers heat to a heat exchanger system (not shown), or when heating, transfers heat from the heat exchanger system. Moreover, gas can, for example, be delivered to the back-side of substrate 25 via a backside gas system to improve the gas-gap thermal conductance between substrate 25 and substrate holder 20. Such a system can be utilized when temperature control of the substrate is required at elevated or reduced temperatures. In other embodiments, heating elements, such as resistive heating elements, or thermoelectric heaters/coolers can be included.

Plasma processing chamber 10 can, for example, further comprise a vertical translational device (not shown) surrounded by a bellows (not shown) coupled to the substrate holder 20 and the plasma processing chamber 10, and configured to seal the vertical translational device from the reduced pressure atmosphere in plasma processing chamber 10. Additionally, a bellows shield (not shown) can, for example, be coupled to the substrate holder 20 and configured to protect the bellows from the processing plasma. Substrate holder 20 can, for example, further provide a focus ring (not shown), a shield ring (not shown), and a baffle plate (not shown).

In the illustrated embodiment, shown in FIG. 2, substrate holder 20 can comprise an electrode through which RF power is coupled to the processing plasma in process space 15. For example, substrate holder 20 can be electrically biased at a RF voltage via the transmission of RF power from a RF generator 40 through an impedance match network 50 to substrate holder 20. The RF bias can serve to heat electrons to form and maintain plasma. In this configuration, the system can operate as a reactive ion etch (RIE) reactor, wherein the chamber and upper gas injection electrode serve as ground surfaces. A typical frequency for the RF bias can range from 1 MHz to 100 MHz and is preferably 13.56 MHz. RF systems for plasma processing are well known to those skilled in the art.

Alternately, RF power is applied to the substrate holder electrode at multiple frequencies. Furthermore, impedance match network 50 serves to increase the transfer of RF power to plasma in plasma processing chamber 10 by minimizing the reflected power. Match network topologies (e.g. L-type, π-type, T-type, etc.) and automatic control methods are well known to those skilled in the art.

With continuing reference to FIG. 2, process gas can be, for example, introduced to processing region 15 through gas injection system (not shown). Process gas can, for example, include a mixture of gases such as argon, $CF_4$ and $O_2$, or argon, $C_4F_8$ and $O_2$ for oxide etch applications, or other chemistries such as $O_2/CO/Ar/C_4F_8$, $O_2/CO/Ar/C_5F_8$, $O_2/CO/Ar/C_4F_6$, $O_2/Ar/C_4F_6$, $O_2/Ar/C_5F_8$, $N_2/H_2$. The gas injection system can include a showerhead, where process gas is supplied from a gas delivery system (not shown) to the processing region 15 through a gas injection plenum (not shown), a series of baffle plates (not shown) and a multiorifice showerhead gas injection plate (not shown). Gas injection systems are well-known to those skilled in the-art of vacuum processing.

Vacuum pump system 30 can, for example, include a turbo-molecular vacuum pump (TMP) capable of a pumping speed up to 5000 liters per second (and greater) and a gate valve for throttling the chamber pressure. In conventional plasma processing devices utilized for dry plasma etch, a 1000 to 3000 liter per second TMP is generally employed. TMPs are useful for low pressure processing, typically less than 50 mTorr. At higher pressures, the TMP pumping speed falls off dramatically. For high pressure processing (i.e., greater than 100 mTorr), a mechanical booster pump and dry roughing pump can be used. Furthermore, a device for monitoring chamber pressure (not shown) can be coupled to the plasma processing chamber 10. The pressure measuring device can be, for example, a Type 628B Baratron absolute capacitance manometer commercially available from MKS Instruments, Inc. (Andover, Mass.).

Controller 14 comprises a microprocessor, memory, and a digital I/O port capable of generating control voltages sufficient to communicate and activate inputs to plasma processing system 1 as well as monitor outputs from plasma processing system 1. Moreover, controller 14 can be coupled to and can exchange information with RF generator 40, impedance match network 50, the gas injection system (not shown), vacuum pump system 30, as well as the backside gas delivery system (not shown), the substrate/substrate holder temperature measurement system (not shown), and the electrostatic clamping system (not shown). For example, a program stored in the memory can be utilized to activate the inputs to the aforementioned components of plasma processing system 1 according to a stored process recipe. One example of controller 14 is a DELL PRECISION WORKSTATION 610™, available from Dell Corporation, Austin, Tex.

The diagnostic system 12 can include an optical diagnostic subsystem (not shown). The optical diagnostic subsystem can comprise a detector such as a (silicon) photodiode or a photomultiplier tube (PMT) for measuring the light intensity emitted from the plasma. The diagnostic system 12 can further include an optical filter such as a narrow-band interference filter. In an alternate embodiment, the diagnostic system 12 can include at least one of a line CCD (charge coupled device), a CID (charge injection device) array, and a light dispersing device such as a grating or a prism. Additionally, diagnostic system 12 can include a monochromator (e.g., grating/detector system) for measuring light at a given wavelength, or a spectrometer (e.g., with a rotating grating) for measuring the light spectrum such as, for example, the device described in U.S. Pat. No. 5,888,337.

The diagnostic system 12 can include a high resolution OES sensor from Peak Sensor Systems, or Verity Instruments, Inc. Such an OES sensor has a broad spectrum that spans the ultraviolet (UV), visible (VIS), and near infrared (NIR) light spectrums. The resolution is approximately 1.4 Angstroms, that is, the sensor is capable of collecting 5550 wavelengths from 240 to 1000 nm. For example, the OES sensor can be equipped with high sensitivity miniature fiber optic UV-VIS-NIR spectrometers which are, in turn, integrated with 2048 pixel linear CCD arrays.

The spectrometers receive light transmitted through single and bundled optical fibers, where the light output from the optical fibers is dispersed across the line CCD array using a fixed grating. Similar to the configuration described above, light emitting through an optical vacuum window is focused onto the input end of the optical fibers via a convex spherical lens. Three spectrometers, each specifically tuned for a given spectral range (UV, VIS and NIR), form a sensor for a process chamber. Each spectrometer includes an independent A/D converter. And lastly, depending upon the sensor utilization, a full emission spectrum can be recorded every 0.1 to 1.0 seconds.

Figure 3:
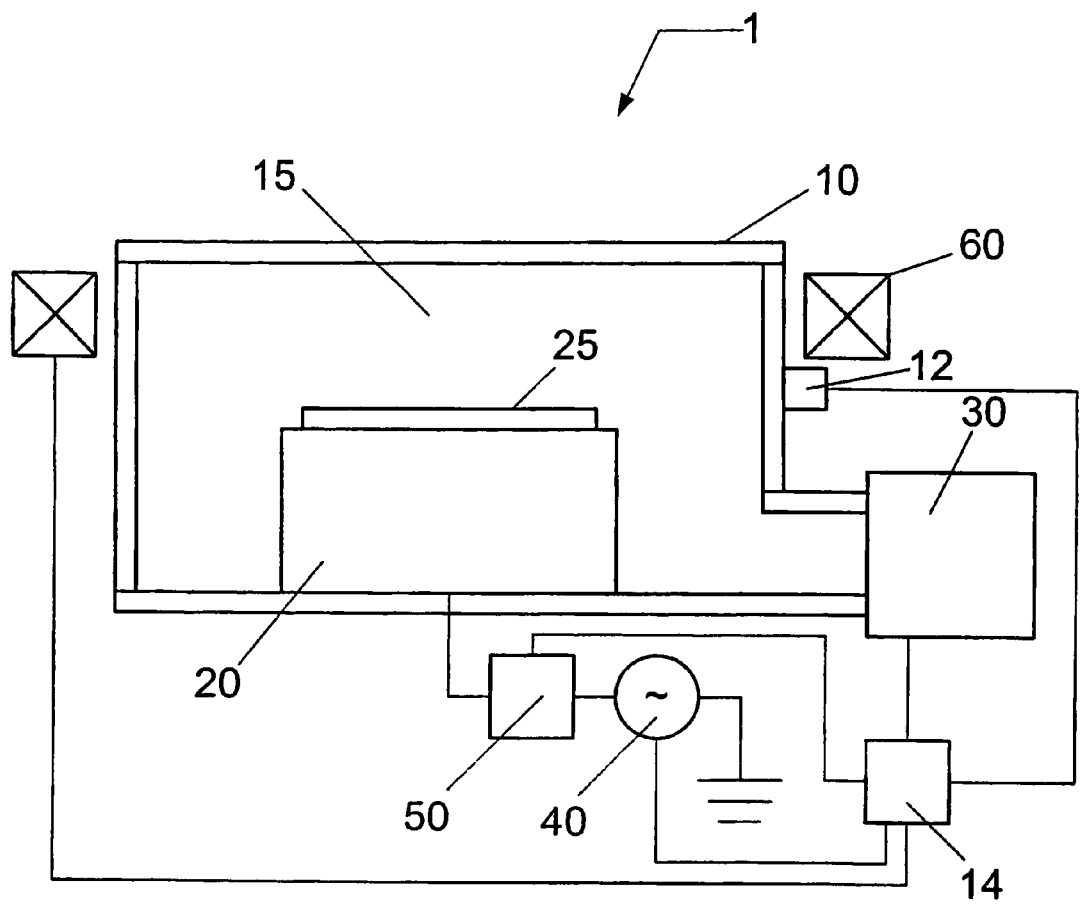
FIG. 3 shows a schematic diagram of a plasma processing system according to another embodiment of the present invention.

In the illustrated embodiment, shown in FIG. 3, the plasma processing system 1 can, for example, further comprise either a stationary, or mechanically or electrically rotating magnetic field system 60, in order to potentially increase plasma density and/or improve plasma processing uniformity, in addition to those components described with reference to FIGS. 1 and 2. Moreover, controller 14 is coupled to magnetic field system 60 in order to regulate the speed of rotation and field strength. The design and implementation of a rotating magnetic field is well known to those skilled in the art.

Figure 4:
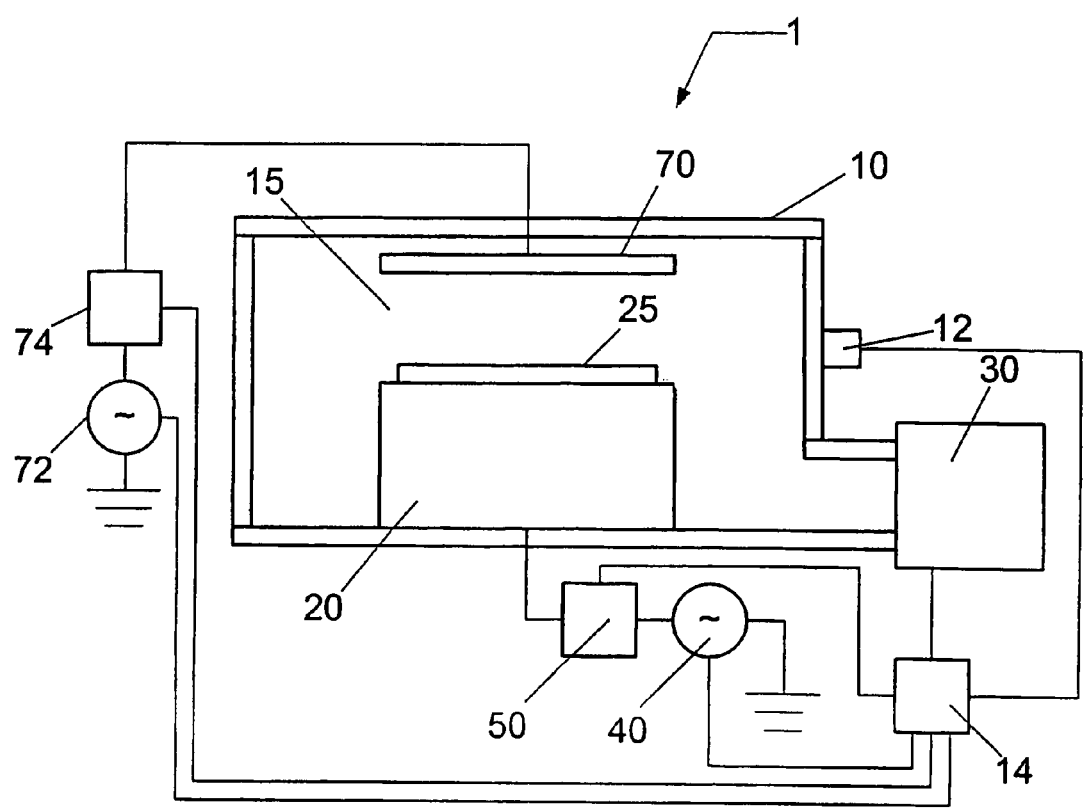
FIG. 4 shows a schematic diagram of a plasma processing system according to another embodiment of the present invention.

In the illustrated embodiment, shown in FIG. 4, the plasma processing system 1 of FIGS. 1 and 2 can, for example, further comprise an upper electrode 70 to which RF power can be coupled from RF generator 72 through impedance match network 74. A typical frequency for the application of RF power to the upper electrode can range from 10 MHz to 200 MHz and is preferably 60 MHz. Additionally, a typical frequency for the application of power to the lower electrode can range from 0.1 MHz to 30 MHz and is preferably 2 MHz. Moreover, controller 14 is coupled to RF generator 72 and impedance match network 74 in order to control the application of RF power to upper electrode 70. The design and implementation of an upper electrode is well known to those skilled in the art.

Figure 5:
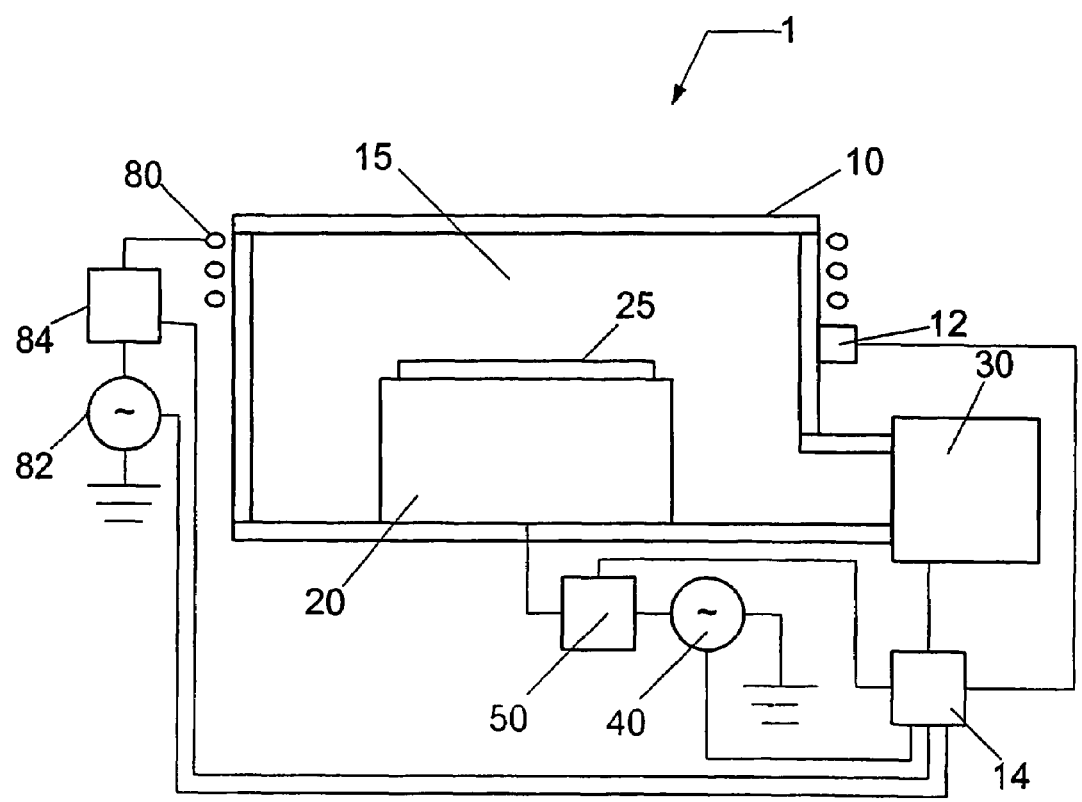
FIG. 5 shows a schematic diagram of a plasma processing system according to another embodiment of the present invention.

In the illustrated embodiment, shown in FIG. 5, the plasma processing system of FIG. 1 can, for example, further comprise an inductive coil 80 to which RF power is coupled via RF generator 82 through impedance match network 84. RF power is inductively coupled from inductive coil 80 through dielectric window (not shown) to plasma processing region 45. A typical frequency for the application of RF power to the inductive coil 80 can range from 10 MHz to 100 MHz and is preferably 13.56 MHz. Similarly, a typical frequency for the application of power to the chuck electrode can range from 0.1 MHz to 30 MHz and is preferably 13.56 MHz. In addition, a slotted Faraday shield (not shown) can be employed to reduce capacitive coupling between the inductive coil 80 and plasma. Moreover, controller 14 is coupled to RF generator 82 and impedance match network 84 in order to control the application of power to inductive coil 80. In an alternate embodiment, inductive coil 80 can be a "spiral" coil or "pancake" coil in communication with the plasma processing region 15 from above as in a transformer coupled plasma (TCP) reactor. The design and implementation of an inductively coupled plasma (ICP) source, or transformer coupled plasma (TCP) source, is well known to those skilled in the art.

Alternately, the plasma can be formed using electron cyclotron resonance (ECR). In yet another embodiment, the plasma is formed from the launching of a Helicon wave. In yet another embodiment, the plasma is formed from a propagating surface wave. Each plasma source described above is well known to those skilled in the art.

Figure 6:
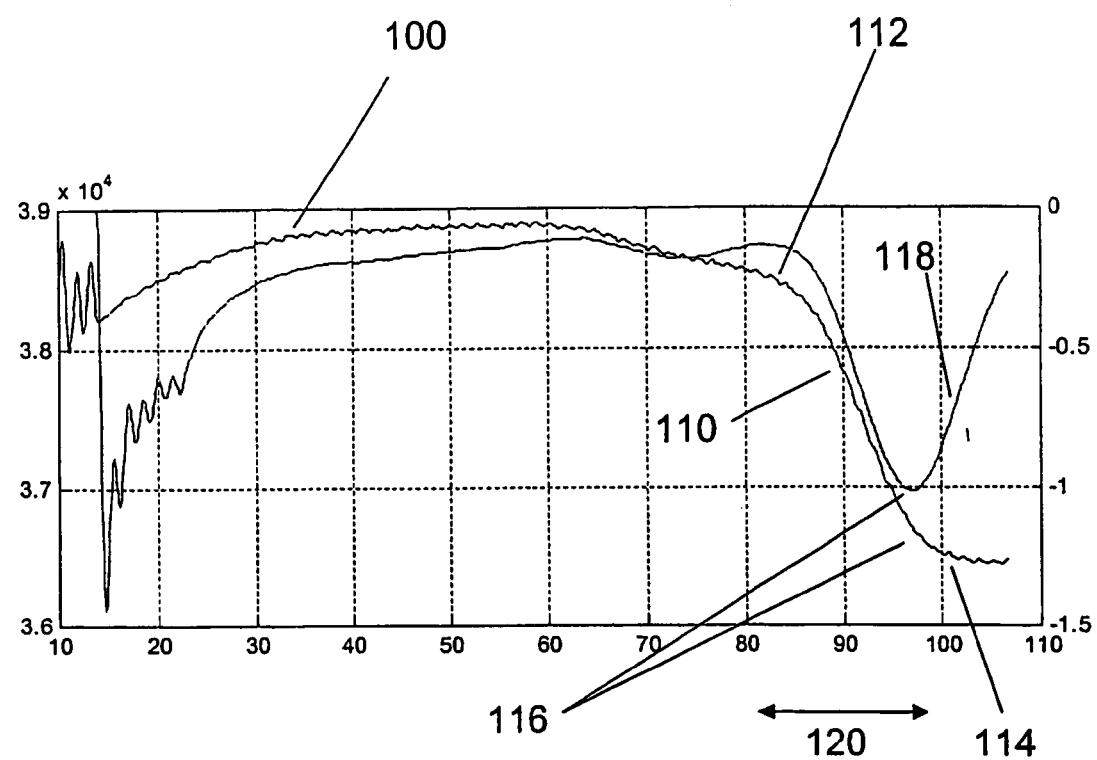
FIG. 6 illustrates an exemplary endpoint signal according to an embodiment of the present invention.

Referring again to FIGS. 1 through 5, diagnostic system 12 can be an optical diagnostic that is utilized to measure the irradiance, or spectral irradiance, of light emitted from the plasma. For example, FIG. 6 presents an exemplary endpoint signal 100 for light of a given wavelength emitted from plasma in the process space 15. The endpoint signal 100 can further comprise an endpoint transition 110, wherein a distinct change in endpoint signal 100 signifies endpoint. For example, light emission corresponding to a specific chemical constituent present during the etch reaction, that either decays (as in FIG. 6) or increases in concentration (and, hence, spectral irradiance) during endpoint, can be selected for monitoring purposes.

By inspection of the endpoint signal 100 in FIG. 6, endpoint can be determined to occur at a start time 112 of the endpoint transition 110, an end time 114 of the endpoint transition 110, or an inflection time 116 of the endpoint transition 110 corresponding to the inflection point in endpoint transition 110. Alternately, a first derivative 118 of the endpoint signal 100 can be computed, and the maximum (in negative slope) of the first derivative 118 of the endpoint transition 110 can be utilized for determining endpoint. Alternately, a second derivative (not shown) of the endpoint signal 100 can be computed, and a zero crossing can be utilized for determining endpoint.

Figure 7A:
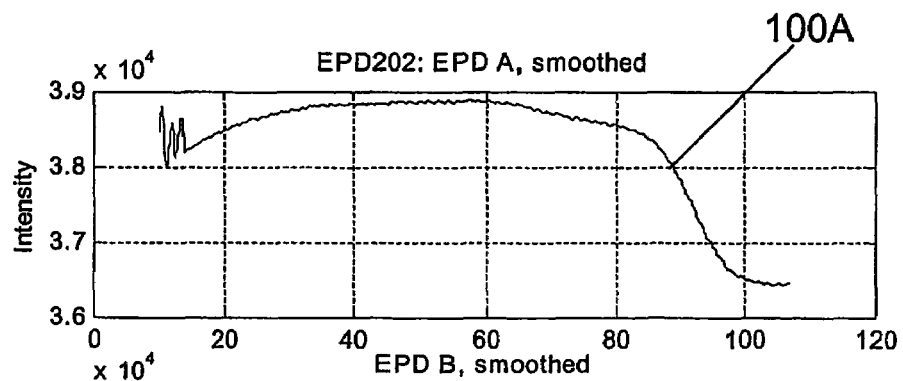
FIGS. 7A-7D illustrate exemplary endpoint signals according to other embodiments of the present invention.
Figure 7B:
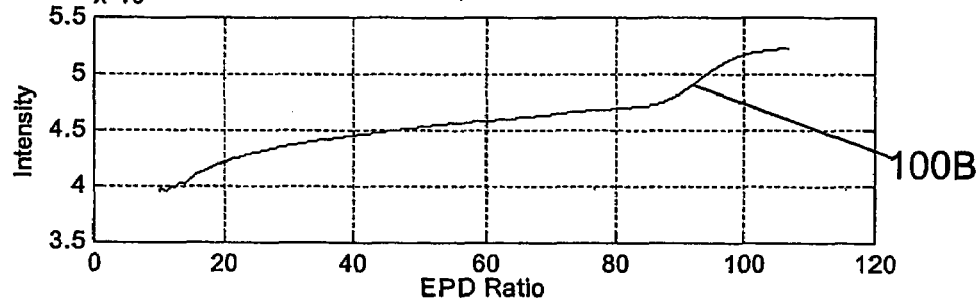
Figure 7C:
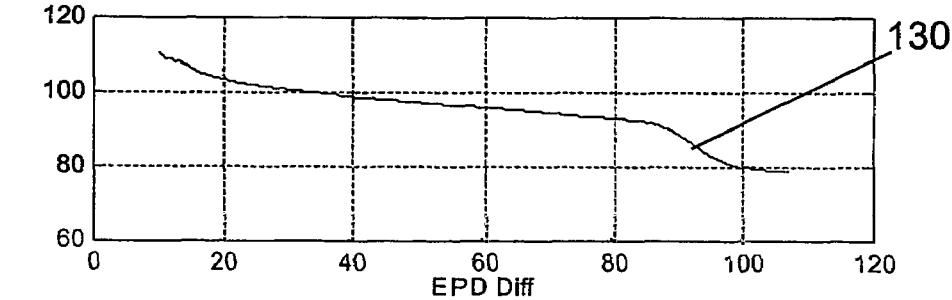
Figure 7D:
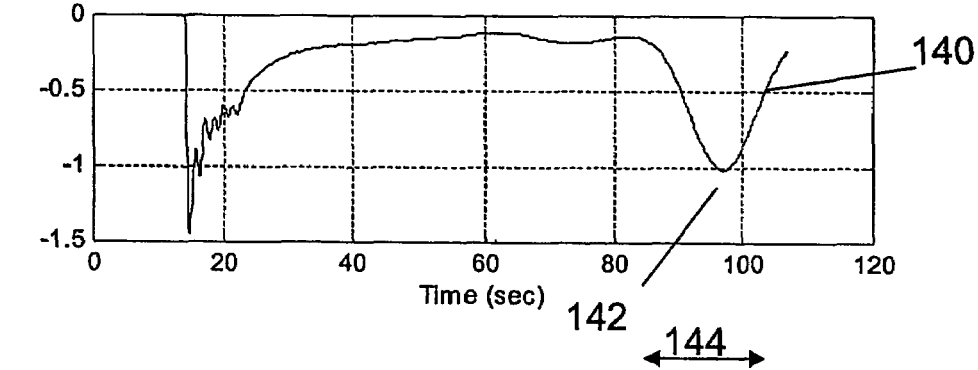

Alternatively, endpoint can be determined from two or more signals from optical diagnostic 12, such as endpoint signals 100A and 100B shown in FIGS. 7A and 7B, respectively. Endpoint signal 100A can, for example, correspond to emission from a chemical constituent whose concentration decays during endpoint, and endpoint signal 100B can, for example, correspond to emission from a chemical constituent whose concentration rises during endpoint. Referring to FIGS. 7C and 7D, one or more ratio signals can then be determined from the two or more endpoint signals (100A, 100B). For example, a ratio signal 130 (FIG. 7C) can be determined by dividing endpoint signal 100A by endpoint signal 100B at each instant in time. Furthermore, one or more differential signals can be determined from the one or more ratio signals. For example, a differential signal 140 (FIG. 7D) determined from a first derivative of the ratio signal 130. The first derivative can be estimated using a first order (forward or backward) difference scheme, or a second order (central) difference scheme. As described above, an endpoint can be determined from the inflection time corresponding to the inflection point in ratio signal 130 or the maximum 142 (in negative slope) of the differential signal 140.

However, the endpoint signal, as depicted in FIG. 6 (100) and FIGS. 7A and 7B (100A, 100B), can be subject to noise and, hence, in some cases the signal-to-noise ratio can be low. Typically, the signal-to-noise ratio can be low when noise, inherent to the plasma processing system, is imposed on the endpoint signal. For example, referring to FIG. 3, the plasma processing system 1 can comprise a transverse magnetic field B, formed by the magnetic field system 60, that is substantially perpendicular to the respective electric field E established by the electrical bias applied to the substrate holder 20. As a result of EXB drift, electrons in the plasma can drift to the side of the process region 15 in the direction of the cross product of the electric E and magnetic B fields. Subsequently, an increased plasma density is observed in this location of the process region 15. When the magnetic field, generated by the magnetic field system 60, is rotating, the off-center peak in plasma density is rotated through the process region 15. As a result of this rotation in the plasma, the diagnostic system 12 observes a periodic fluctuation in intensity, such as when using optical emission spectroscopy (OES).

Figure 8A:
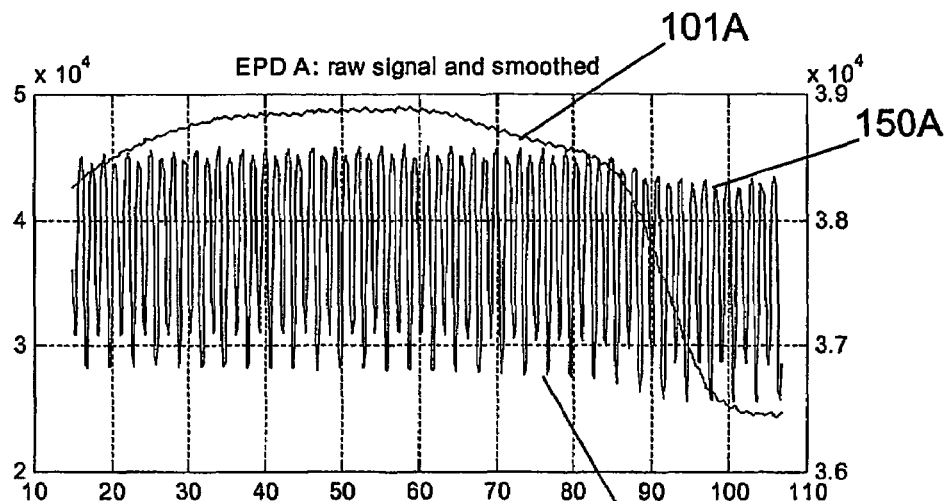
FIGS. 8A and 8B illustrate an exemplary raw and filtered endpoint signal according to another embodiment of the present invention.
Figure 8B:
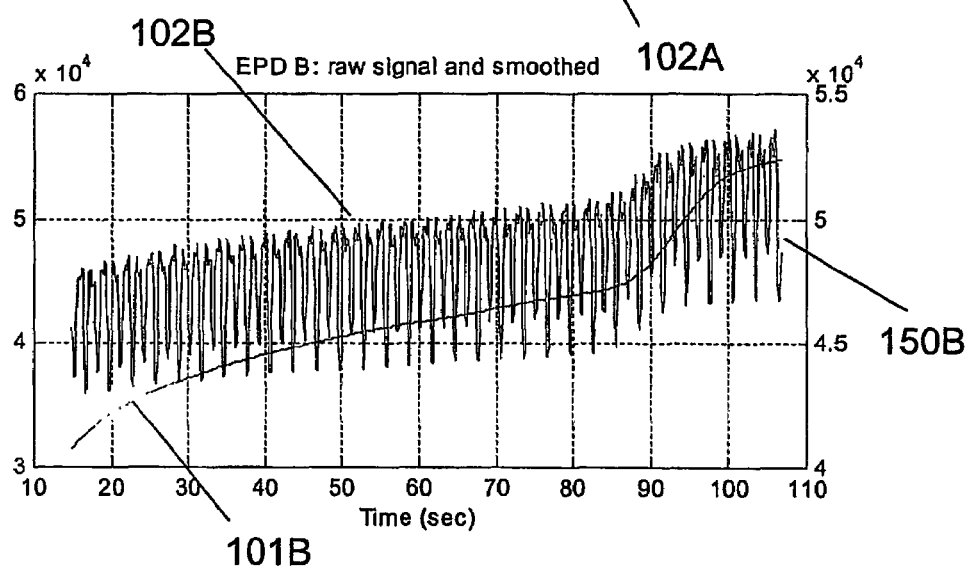

For example, FIGS. 8A and 8B present typical raw endpoint signals 101A, 101B, and corresponding smoothed endpoint signals 150A, 150B that are computed using a moving average. The fluctuations 102A and 102B in the endpoint signals 101A and 101B correspond to the effect the rotating magnetic field has on the plasma in process space 15. The frequency of the fluctuation 102A and 102B are associated with the rotation frequency of the magnetic field.

In the case where one or more endpoint signals and a first derivative of a subsequent signal (such as a ratio signal) are used, it is necessary to impose some smoothing (or filtering) of the signals during post-processing in order to alleviate the above identified noise and identify an endpoint. However, in order to achieve accurate endpoint detection, the post-processing steps utilized must preserve the dynamic range of variations embedded within the endpoint signal(s).

A method to reduce noise in a one-dimensional stream of data (e.g. time-series, spectrum), and retain the dynamic range of variations in the data is to apply a least squares smoothing polynomial filter, also referred to as the Savitzky-Golay (SG) finite impulse response (FIR) smoothing filter, cf. Numerical Recipes (Press et al. 1992, Sec. 14.8) (the contents of which are incorporated herein by reference). In general, the SG filters out-perform standard averaging FIR filters, which tend to remove a significant portion of the signal's high frequency content along with the noise. SG filters are typically employed to remove noise from a signal comprising a broadband frequency spectrum, and they are optimal in the sense that they minimize the least squares error in fitting a polynomial to windows of data. The low-pass filter coefficients of the SG filter are computed by effectively least-squares fitting a polynomial in a moving window, centered on each data point, so that the new value for each data point will be the zeroth coefficient of the polynomial. Approximate first derivatives of the data can be computed by using the first order coefficient of each polynomial, and so on. The filter coefficients for a specified polynomial order and filter window width are computed independent of any data, and stored. Thereafter, the SG filter is convolved with the data to provide a smoothed data stream with reduced noise, however, retaining higher order variations. The utilization of other smoothing techniques, such as moving averages, does not preserve the higher order variations in the data stream. Algorithms implementing SG filters for post-processing data are commercially available through MATLAB, available from The Mathworks, Inc. (3 Apple Hill Drive, Natick, Mass. 01760-2098).

Referring again to FIGS. 7A and 7B, endpoint signals 100A and 100B are smoothed using running averages, and the differential signal 140 (FIG. 7D) is computed from the ratio signal 130 (FIG. 7C) using simple differencing and additional smoothing. As a consequence, the time duration 144 of the endpoint transition is unduly broadened and the peak 142 of the endpoint transition is offset to a later time.

In order to illustrate the advantages of the SG filter, FIGS. 9A1-9D1 present a number of manipulations of the endpoint signals 150A and 150B (FIGS. 8A and 8B) using various post-processing techniques. Ratio signal 130 (FIG. 9A1) comprises a ratio of the smoothed endpoint signals 100A and 100B of FIGS. 7A and 7B, wherein the smoothing is imposed using moving averages. Differential signal 160 (FIG. 9A2) represents a simple difference of the ratio signal 130. The time duration and peak of the endpoint transition are captured within differential signal 160, however, they are immersed within the noise remnants not removed during the smoothing of the raw endpoint signals.

Differential signal 162 (FIG. 9B1) represents a moving average of differential signal 160 (using a moving window of 29 data points). From inspection of differential signal 162, the time duration of the endpoint transition is expanded and the peak of the endpoint transition is shifted to a greater time relative to differential signal 160. Differential signal 164

(FIG. 9B2) represents the application of a finite impulse response (FIR) filter to differential signal 162 and, by inspection, the broadening of the time duration and the shifting of the peak are exacerbated.

Differential signal 166 (FIG. 9C1) represents the application of a Savitsky Golay (SG) filter to the ratio signal 130 using a second degree polynomial fit and a filter window width of 11 data points. By inspection, the performance relative to differential signal 160 is improved; however, noise still remains on the signal. Differential signal 168 (FIG. 9C2) further smooths differential signal 166 by imposing a moving average; however, it suffers from some of the above identified problems.

Differential signal 170 (FIG. 9D1) represents the application of a SG filter to the ratio signal 130 using a first degree polynomial fit and a filter window of 29 data points. The resultant signal is considerably improved, with regards to the time duration of the endpoint transition and the peak of the endpoint transition, and, by inspection, compares favorably with differential signal 160.

Figure 10:
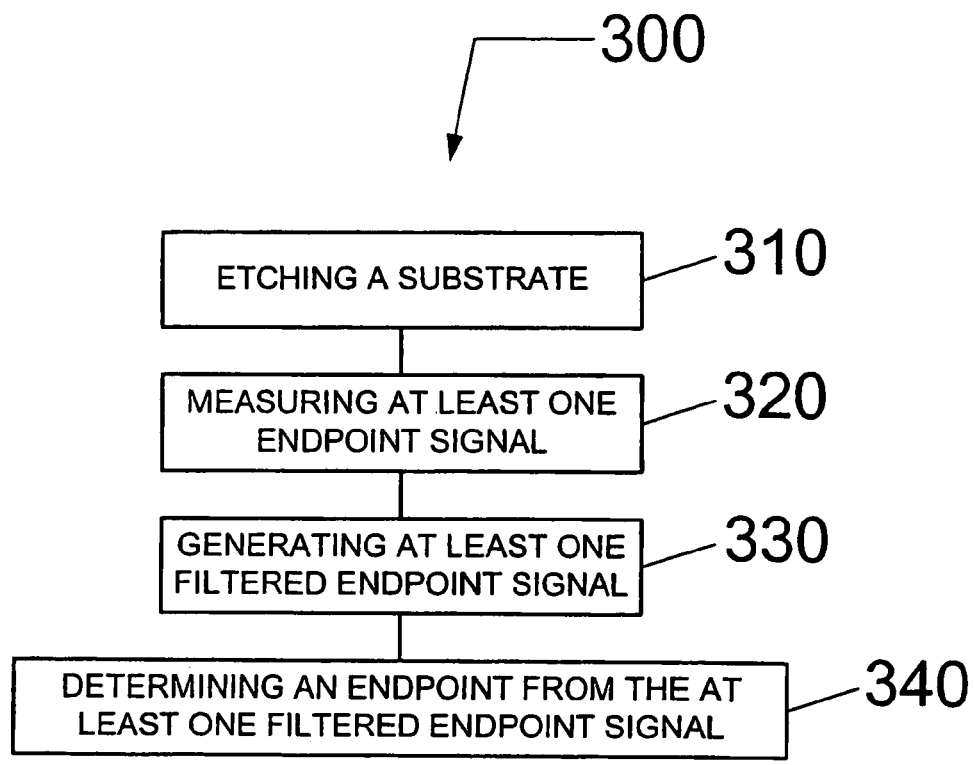
FIG. 10 presents a method of determining an endpoint of an etch process in a plasma processing system according to an embodiment of the present invention.

FIG. 10 presents a method for detecting an endpoint of an etch process for etching a substrate in a plasma processing system according to an embodiment of the present invention. The method is illustrated in a flowchart 300 beginning in step 310 with etching a substrate in the plasma processing system, such as the systems described in reference to FIGS. 1 through 5. The substrate can, for example, be a circular wafer, or a rectangular display.

In step 320, at least one endpoint signal is measured. Each endpoint signal can, for example, comprise endpoint transition, wherein a distinct change in the endpoint signal signifies endpoint. Furthermore, the endpoint signal can comprise an optical signal acquired using an optical diagnostic subsystem, wherein the optical diagnostic subsystem comprises at least one of a detector, an optical filter, a grating, a prism, a monochromator, a spectrometer, a charge coupled device (CCD) array, and a charge injection device (CID) array.

In step 330, at least one endpoint signal is filtered to generate at least one filtered endpoint signal. The filter utilized to generate the at least one filtered endpoint signal can comprise a Savitsky Golay filter, wherein the applying the filter comprises setting a filter window width and a polynomial order as described above. For example, the filter window width can be an odd integer, and it can range from a value of 9 to 109. Furthermore, the filter window width can represent a fraction of the data stream length, i.e. 0.01% to 5% of the number of acquired data points in the data stream. Additionally, for example, the polynomial order can range from 1 to 4, and, desirably, the polynomial order is unity. The at least one filtered endpoint signal can, for example, comprise at least one smoothed endpoint signal, or it can comprise at least one smoothed first derivative of the endpoint signal, or at least one smoothed second derivative of the endpoint signal.

In step 340, an endpoint of the process is determined from the at least one filtered endpoint signal. In general, each filtered endpoint signal can comprise an endpoint transition, wherein the endpoint transition is utilized to determine endpoint. For example, the endpoint can be determined at a start time of the endpoint transition, an end time of the endpoint transition, and an inflection time of the endpoint transition as described above. Alternatively, the at least one filtered endpoint signal can comprise a first filtered endpoint signal and a second filtered endpoint signal. A ratio signal can be determined from a ratio of the first and second filtered endpoint signals. Thereafter, the endpoint can be determined from the endpoint transition in the ratio signal using the techniques described above. Alternatively, a differential signal can be determined from the ratio signal, wherein the differential signal comprises at least one of a first derivative and a second derivative of the ratio signal. The derivatives can be determined using,simple differencing, or a Savitsky Golay filter. Thereafter, the endpoint can be determined from the endpoint transition in the differential signal using the techniques described above.

Figure 11:
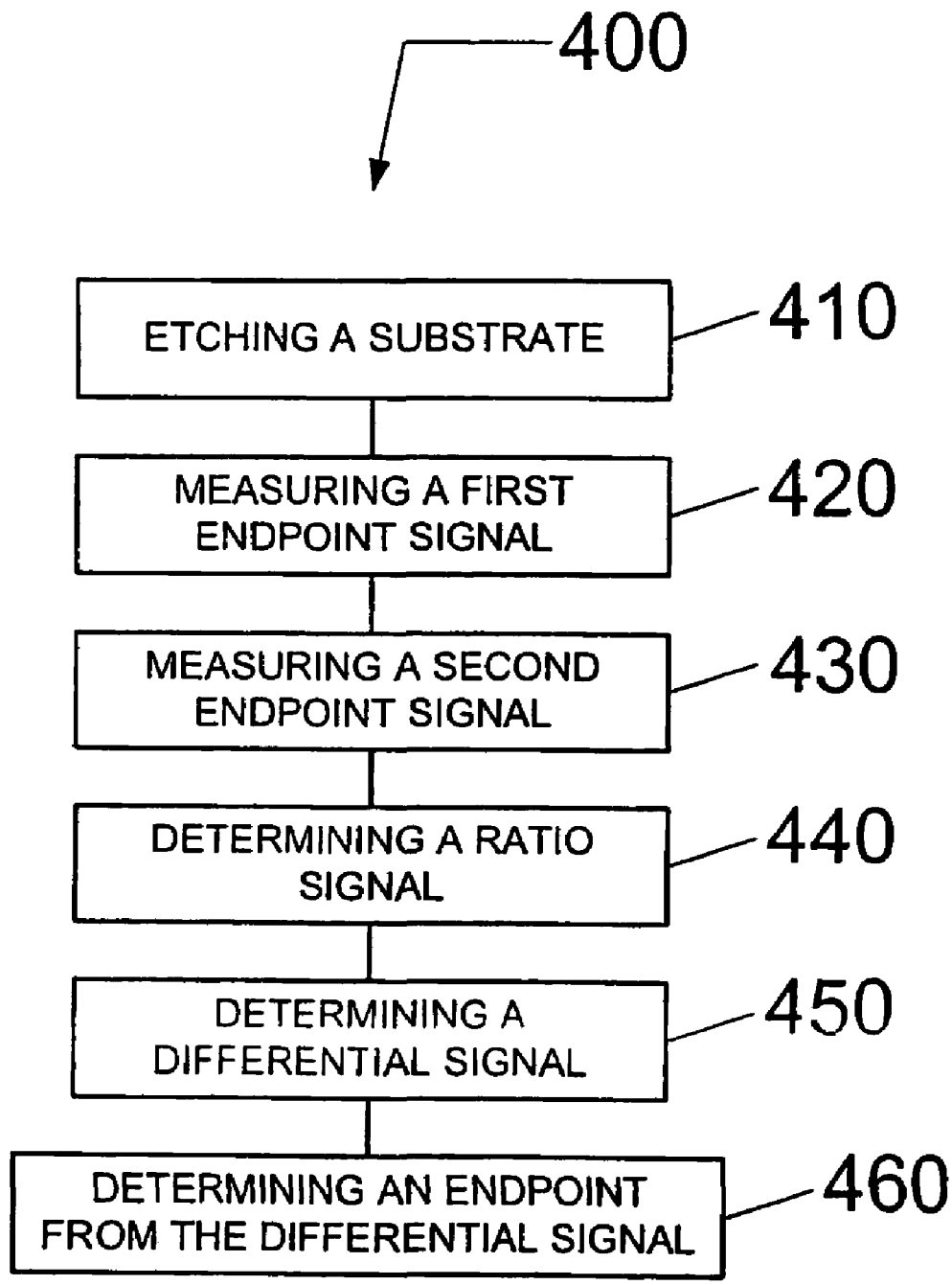
FIG. 11 presents a method of determining an endpoint of an etch process in a plasma processing system according to another embodiment of the present invention.

FIG. 11 presents a method for detecting an endpoint of an etch process for etching a substrate in a plasma processing system according to another embodiment of the present invention. The method is illustrated in a flowchart 400 beginning in step 410 with etching a substrate in the plasma processing system, such as the systems described in reference to FIGS. 1 through 5. The substrate can, for example, be a circular wafer, or a rectangular display.

In step 420, a first endpoint signal is measured. The first endpoint signal can, for example, comprise an endpoint transition, wherein a distinct change in the endpoint signal signifies endpoint. Furthermore, the first endpoint signal can comprise an optical signal acquired using an optical diagnostic, wherein the optical diagnostic comprises at least one of a detector, an optical filter, a grating, a prism, a monochromator, a spectrometer, a charge coupled device (CCD) array, and a charge injection device (CID) array.

In step 430, a second endpoint signal is measured. The second endpoint signal can, for example, comprise an endpoint transition, wherein a distinct change in the endpoint signal signifies endpoint. Furthermore, the second endpoint signal can comprise an optical signal acquired using an optical diagnostic, wherein the optical diagnostic comprises at least one of a detector, an optical filter, a grating, a prism, a monochromator, a spectrometer, a charge coupled device (CCD) array, and a charge injection device (CID) array.

In step 440, a ratio signal is determined from a ratio of the first endpoint signal and the second endpoint signal at each instant in time.

In step 450, a differential signal is determined from the ratio signal by applying a differential filter, wherein the differential filter comprises a Savitsky Golay filter. The application of the Savitsky Golay filter further comprises setting a filter window width and a polynomial order. Furthermore, the filter window width can represent a fraction of the data stream length, i.e. 0.01% to 5% of the number of acquired data points in the data stream. Additionally, for example, the polynomial order can range from 1 to 4, and, desirably, the polynomial order is unity.

In step 460, an endpoint of the process is determined from the differential signal, wherein the differential signal comprises an endpoint transition. For example, the endpoint can be determined at a start time of the endpoint transition, an end time of the endpoint transition, and an inflection time of the endpoint transition as described above.

Alternately, in steps 420 and 430, the first and second endpoint signals can be filtered using at least one of a moving average, a finite impulse response filter, and a Savitsky Golay filter.

Although only certain exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A method for detecting an endpoint of a process in a plasma processing system comprising:
   starting said process in a process chamber;
   measuring at least two endpoint signals;
   generating at least two filtered endpoint signals by applying a Savitsky Golay filter to said at least two endpoint signals; and
   determining an endpoint of said process from said at least two filtered endpoint signals,
   wherein said at least two filtered endpoint signals comprise a first filtered endpoint signal corresponding to a first chemical constituent found in the process chamber and a second filtered endpoint signal corresponding to a second chemical constituent found in the process chamber,
   wherein said endpoint is determined from a ratio signal, said ratio signal generated by a ratio of said first filtered endpoint signal and said second filtered endpoint signal,
   wherein the first filtered signal corresponds to a first chemical constituent whose concentration decays during endpoint, and
   wherein the second filtered signal corresponds to a second chemical constituent whose concentration rises during endpoint.

2. The method as recited in claim 1, wherein said at least two filtered endpoint signals each comprise a smoothed endpoint signal.

3. The method as recited in claim 1, wherein said at least two filtered endpoint signals comprise at least one of a smoothed first derivative of each of said at least two endpoint signals, and a smoothed second derivative of each of said at least two endpoint signals.

4. The method as recited in claim 1, wherein said ratio comprises an endpoint transition.

5. The method as recited in claim 4, wherein said determining said endpoint from said at least two filtered endpoint signals comprises using at least one of a start time of said endpoint transition, an end time of said endpoint transition, and an inflection time of said endpoint transition.

6. The method as recited in claim 1, wherein said at least two endpoint signals comprise optical signals from said plasma processing system.

7. The method as recited in claim 6, wherein said optical signals are related to a spectral irradiance of emitted light from said plasma processing system.

8. The method as recited in claim 6, wherein said optical signals are measured using an optical diagnostic subsystem, said optical diagnostic subsystem comprising at least one of a detector, an optical filter, a grating, a prism, a monochromator, a spectrometer, a CCD array, and a CID array.

9. The method as recited in claim 1, wherein said endpoint is determined from a differential signal, said differential signal comprising at least one of a first derivative, and a second derivative of said ratio signal.

10. The method as recited in claim 1, wherein said applying said Savitsky Golay filter comprises setting a filter window width and a polynomial order.

11. The method as recited in claim 1, wherein the first filtered endpoint signal corresponds to an emission intensity of light at a first wavelength corresponding to the first chemical constituent found in the process chamber, and
   the second filtered endpoint signal corresponds to an emission intensity of light at a second wavelength corresponding to the second chemical constituent found in the process chamber.

12. The method as recited in claim 11, wherein each wavelength is measured using optical emission spectroscopy.

13. A method for detecting an endpoint of a process comprising:
   starting said process in a process chamber;
   measuring a first endpoint signal corresponding to a first chemical constituent found in the process chamber;
   measuring a second endpoint signal corresponding to a second chemical constituent found in the process chamber;
   determining a ratio signal from a ratio of said first endpoint signal and said second endpoint signal, said ratio signal comprises an endpoint transition;
   determining a differential signal from said ratio signal by applying a differential filter to said ratio signal, wherein said differential filter comprises a Savitsky Golay filter; and
   determining an endpoint of said process from said differential signal,
   wherein the first filtered signal corresponds to a first chemical constituent whose concentration decays during endpoint, and
   wherein the second filtered signal corresponds to a second chemical constituent whose concentration rises during endpoint.

14. The method as recited in claim 13, wherein said measuring said first endpoint signal further comprises filtering said first endpoint signal, said filtering comprising at least one of a moving average, a finite impulse response filter, and a Savitsky Golay filter.

15. The method as recited in claim 14, wherein said measuring said second endpoint signal further comprises filtering said second endpoint signal, said filtering comprising at least one of a moving average, a finite impulse response filter, and a Savitsky Golay filter.

16. The method as recited in claim 13, wherein each of said first endpoint signal and said second endpoint signal comprise optical signals from a plasma process.

17. The method as recited in claim 16, wherein each of said optical signals is related to a spectral irradiance of emitted light from said plasma process.

18. The method as recited in claim 16, wherein said optical signals are measured using an optical diagnostic subsystem, said optical diagnostic subsystem comprising at least one of a detector, an optical filter, a grating, a prism, a monochromator, a spectrometer, a CCD array, and a CID array.

19. The method as recited in claim 13, wherein said applying said differential filter comprises setting a filter window width and a polynomial order.

20. The method as recited in claim 13, wherein said differential signal comprises at least one of a first derivative of said ratio signal and a second derivative of said ratio signal.

21. The method as recited in claim 13, wherein said determining said endpoint comprises using at least one of a start time of said endpoint transition, an end time of said endpoint transition, and an inflection time of said endpoint transition.

22. The method as recited in claim 13, wherein the first filtered endpoint signal corresponds to an emission intensity of light at a first wavelength corresponding to the first chemical constituent found in the process chamber, and
   the second filtered endpoint signal corresponds to an emission intensity of light at a second wavelength corresponding to the second chemical constituent found in the process chamber.

23. The method as recited in claim 22, wherein each wavelength is measured using optical emission spectroscopy.

24. A plasma processing system comprising:
a process chamber;
a diagnostic system coupled to said process chamber and configured to measure at least two filtered endpoint signals; and
a controller coupled to said diagnostic system, configured to filter said at least two filtered endpoint signals using a Savitsky Golay filter, and configured to determine an endpoint from the filtered endpoint signals,
wherein said at least two filtered endpoint signals comprise a first filtered endpoint signal corresponding to a first chemical constituent found in the process chamber and a second filtered endpoint signal corresponding to a second chemical constituent found in the process chamber,
wherein said controller is configured to determine said endpoint from a ratio signal, said ratio signal generated by a ratio of said first filtered endpoint signal and said second filtered endpoint signal, wherein the first filtered signal corresponds to a first chemical constituent whose concentration decays during endpoint, and
wherein the second filtered signal corresponds to a second chemical constituent whose concentration rises during endpoint.

25. The plasma processing system as recited in claim 24, wherein said diagnostic system comprises an optical diagnostic subsystem.

26. The plasma processing system as recited in claim 25, wherein said optical diagnostic subsystem comprises at least one of a detector, an optical filter, a grating, a prism, a monochromator, a spectrometer, a CCD array, and a CID array.

27. The plasma processing system as recited in claim 24, wherein said ratio comprises an endpoint transition.

28. The plasma processing system as recited in claim 27, wherein said controller is further configured to determine said endpoint from said at least two filtered endpoint signals using at least one of a start time of said endpoint transition, an end time of said endpoint transition, and an inflection time of said endpoint transition.

29. The plasma processing system as recited in claim 24, wherein said controller is configure to determine said endpoint from a differential signal, said differential signal comprising at least one of a first derivative, and a second derivative of said ratio signal.

30. The plasma processing system as recited in claim 24, wherein said Savitsky Golay filter comprises a filter window width and a polynomial order.

31. The system as recited in claim 24, wherein the first filtered endpoint signal corresponds to an emission intensity of light at a first wavelength corresponding to the first chemical constituent found in the process chamber, and
the second filtered endpoint signal corresponds to an emission intensity of light at a second wavelength corresponding to the second chemical constituent found in the process chamber.

32. The system as recited in claim 31, wherein each wavelength is measured using optical emission spectroscopy.

* * * * *